US008831733B2

(12) United States Patent
Wilke et al.

(10) Patent No.: US 8,831,733 B2
(45) Date of Patent: Sep. 9, 2014

(54) BRAIN REPAIR USING ELECTRICAL STIMULATION OF HEALTHY NODES

(71) Applicant: California Institute of Technology, Pasadena, CA (US)

(72) Inventors: Melanie Wilke, Goettingen (DE); Igor Kagan, Goettingen (DE); Richard A. Andersen, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/943,227

(22) Filed: Jul. 16, 2013

(65) Prior Publication Data

US 2014/0018882 A1    Jan. 16, 2014

Related U.S. Application Data

(60) Provisional application No. 61/672,108, filed on Jul. 16, 2012.

(51) Int. Cl.
*A61N 1/00* (2006.01)
*A61N 1/36* (2006.01)

(52) U.S. Cl.
CPC .................................. *A61N 1/36103* (2013.01)
USPC ............................................................ 607/45

(58) Field of Classification Search
USPC ............................................................ 607/45
See application file for complete search history.

(56) References Cited

U.S. PATENT DOCUMENTS

2012/0209350 A1* 8/2012 Taylor et al. .................... 607/54

OTHER PUBLICATIONS

Wilke, et al., "Functional imaging reveals rapid reorganization of cortical activity after parietal inactivation in monkeys,"<http://www.pnas.org/cgi/doi/10.1073/pnas.1204789109>, PNAS, vol. 109, No. 21 (May 22, 2012).
Wilke, et al. "Effects of Pulvinar Inactivation on Spatial Decision-making between Equal and Asymmetric Reward Options." Journal of Cognitive Neuroscience 25:8, pp. 1270-1283. (2013).
Hwang, et al. "Inactivation of the Parietal Reach Region Causes Optic Ataxia, Impairing Reaches but not Saccades." Neuron Article 76, pp. 1021-1029 (Dec. 6, 2012).
Kagan I, Iyer A. Lindner A, & Andersen RA (2010) "Space representation for eye movements is more contralateral in monkeys than in humans." Proc Natl Acad Sci U S A 107(17):7933-7938.
Andersen, et al. "Natural and Accelerated Recovery From Brain Damage," IEEE Pulse, 61-65 (Mar./Apr. 2012).

\* cited by examiner

*Primary Examiner* — George Manuel
(74) *Attorney, Agent, or Firm* — Wayne L. Tang; Nixon Peabody LLP (57) ABSTRACT

A method and system of compensating for a damaged brain node is disclosed. The damaged node is determined by techniques such as fMRI or neural recording. A healthy node that can compensate for the function of the damaged node is determined. A stimulating electrode is placed on at least one functioning node to bypass the activity from the damaged node to compensate for a missing node. The functioning node is then stimulated to compensate for the damaged node.

22 Claims, 4 Drawing Sheets

BRAIN REPAIR USING ELECTRICAL STIMULATION OF HEALTHY NODES

PRIORITY

The present application claims priority to U.S. Provisional Application 61/672,108 filed on Jul. 16, 2012, which is hereby incorporated by reference in its entirety.

FEDERAL SUPPORT STATEMENT

The subject matter of this invention was made with government support under EY005522 awarded by the National Institutes of Health and under N660011-10-C-2009 awarded by the Space and Naval Warfare Systems. The government has certain rights in the invention.

COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

TECHNICAL FIELD

The present disclosure relates generally to compensating for deficits in the brain and specifically electrically stimulating functioning nodes in a brain circuit to compensate for damaged nodes.

BACKGROUND

Brain functions typically involve precise circuits with nodes interconnected over long distances. Thus a brain lesion can interrupt one node in a circuit, leaving the other nodes intact but rendering the overall circuit inoperable. Lesions in the brain typically occur as a result of events such as strokes and traumatic brain injury.

One specific form of brain damage is the deficit of neglect. Neglect is commonly a result of damage to the posterior parietal cortex (PPC). Patients ignore or are not aware of the contralateral space, particularly left space for right parietal damage. A popular competition theory has been proposed for neglect in which the two cerebral hemispheres each process information in the contralateral space and they compete with one another for the distribution of attention and awareness. If one hemisphere is damaged then the other has an advantage and the patient is biased toward the healthy visual field and unable to process information in the unhealthy part of space.

Another deficit is optic ataxia, which is caused by lesions in the human PPC. Optic ataxia (OA) impairs reaches but not saccades (eye movements) to visual objects. It has been suggested that there are separate visuomotor pathways for the two effectors of limbs (reaches) and eyes (saccades). In monkeys, one potentially crucial area for reach control is the parietal reach region (PRR), in which neurons respond preferentially during reach planning as compared to saccade planning. Direct causal evidence linking the monkey PRR to the deficits observed in OA has recently been shown in inactivation studies (Hwang, et al., "Inactivation of the Parietal Reach Region Causes Optic Ataxia, Impairing Reaches but Not Saccades" *Neuron*, Vol. 76, pp. 1021-29, Dec. 6, 2012). Lesions to Brodmann's area 5 also produce OA.

There is therefore a need for a method of brain repair that utilizes healthy nodes to compensate for damaged nodes. There is a further need for a system based on studies of brain circuits to determine likely nodes for stimulation to repair damage from brain lesions resulting in deficits.

SUMMARY

According to one example, a method of brain repair of a damaged node is disclosed. The location of a damaged node within a brain circuit is determined. At least one functioning node to compensate for the damaged node within the brain circuit is determined. A stimulator is placed on the brain on the at least one functioning node to bypass the activity from the damaged node to compensate for a missing node. The at least one functioning node is stimulated to compensate for the damaged node.

Another example is a system for compensating for a damaged node of a brain circuit. The system includes a storage device including data associated with a brain circuit having the damaged node. A controller is coupled to the storage device to select a healthy node to stimulate to bypass the damaged node based on the data associated with the brain circuit and a model of the brain circuit. A stimulator for stimulation of the selected healthy node of the brain circuit is provided. The stimulator is operable to stimulate the healthy nodes to bypass the function of the damaged node.

Additional aspects of the invention will be apparent to those of ordinary skill in the art in view of the detailed description of various embodiments, which is made with reference to the drawings, a brief description of which is provided below.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Figure 1A:
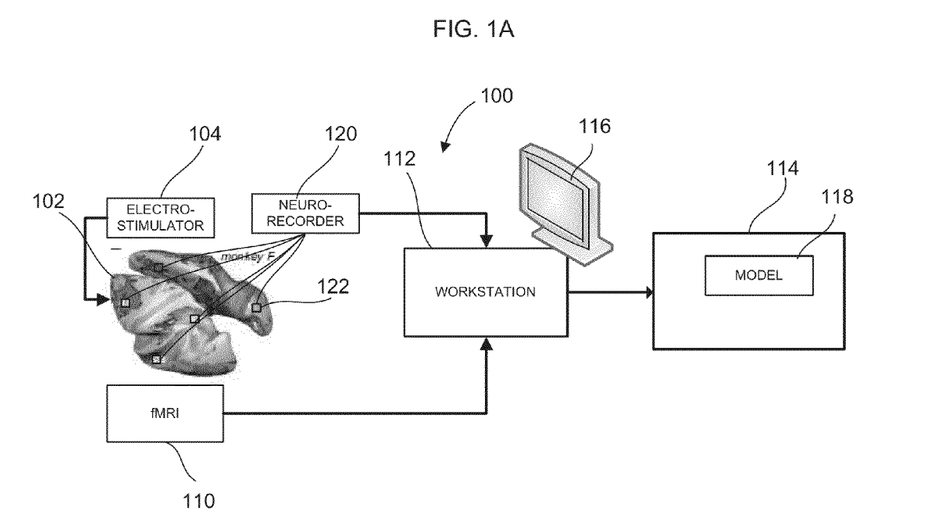
FIG. 1A is a block diagram of a detection and repair system to compensate for damage to brain nodes.

FIG. 1A shows a brain damage detection and repair system 100 that is directed to treatment of a patient by stimulating a brain 102 having a damaged area effecting brain circuits. The system 100 includes a stimulator such as an electrical stimulator system 104 that is implanted in the brain 102. Other types of stimulators such as an optogenetic stimulator applying light stimulation via an optical fiber could be used instead of electrical stimulation. The system 100 includes a functional magnetic resonance imager (fMRI) 110 that is coupled to a workstation 112 having a display 116. The workstation 112 is coupled to a storage device that stores a database 114, data analysis software, and models of the brain as well as data taken from the fMRI imager 110. The fMRI imager 110 is used to scan the brain 102 to determine the location of healthy and damaged nodes in a damaged brain circuit. The workstation 112 runs the data analysis software and accesses the database 114 to analyze the damage in the brain based on a stored model 118 to provide analysis as to the nodes to stimulate in the case of brain damage using the electrical stimulator system 104 implanted in the patient. The system 100 may also have a neural recorder 120, which includes an array of recording electrodes 122 that may be connected to the brain 102 to record impulses in different brain nodes. The neural recorder 120 may also be used to determine the location of healthy and damaged nodes in a damaged brain circuit in addition to or independently of the fMRI imager 110. Additional sensing of the brain 102, such as optical imaging of cell activity, could also be used. Such optical imaging includes use of an optical recorder to record populations of neurons with a node or nodes of the brain circuit.

The system 100 provides a treatment mechanism and procedure for providing recovery from brain lesions by electrical stimulation of functioning nodes of brain circuits. Brain functions typically involve precise circuits with nodes interconnected over long distances in the brain. Thus a brain lesion can interrupt one node in a circuit, leaving the other nodes intact but rendering the overall circuit inoperable for the respective brain function.

Stimulation of the surviving parts of the brain circuit via the electrical stimulator system 104 may restore the function of the damaged nodes in the circuit by compensating for the loss of damaged nodes by healthy nodes. This therapy is effective for conditions caused by brain diseases such as stroke or traumatic brain injury, which may damage or render nodes inoperable. As explained below, functional imaging shows rapid reorganization of cortical activity after parietal inactivation in monkeys and indicates the brain nodes that could be electrically stimulated to reduce deficits from lesion to the parietal cortex.

The system 100 is designed to replace or balance activity with chronic stimulation of the brain 102 for particular neurological deficits from brain injury. One example deficit is neglect, but many cognitive neural deficits may be cured with this approach.

Diagnostics for deciding on the chronic placement of stimulating electrodes from the electrical stimulator system 104 are determined using functional magnetic resonance imaging (fMRI) studies in patients taken from the fMRI imager 110 or signals received from the recording electrodes 122 and displayed on the display 116. Alternatively, the placement of the electrodes may be based on guidance of previous findings in patients with similar deficits or in animal studies. The stimulation from the electrical stimulator system 104 is applied to circuits that are part of the normal functioning of the brain. If one node of the circuit is damaged, then other nodes are stimulated to bypass or balance the activity in the circuit to compensate for the missing node.

Figure 1B:
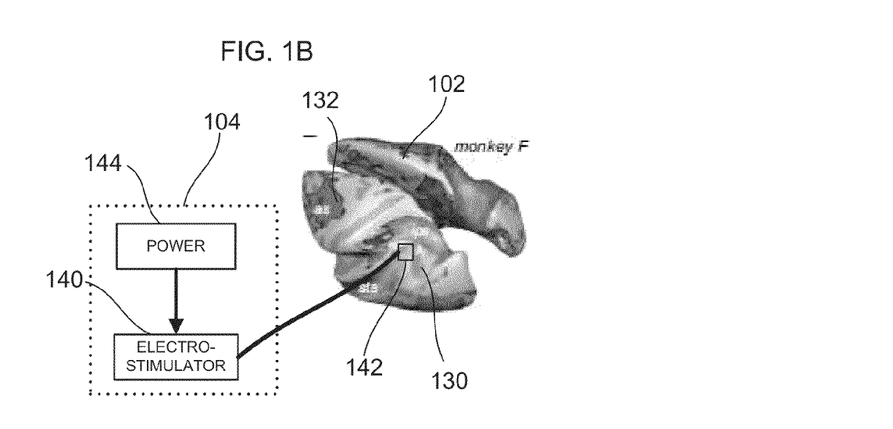
FIG. 1B is a block diagram of an electrode stimulator coupled to a healthy node to compensate for a damaged node to address neglect.

FIG. 1B is a block diagram of the electrical stimulator system 104 in FIG. 1A, which is employed for one specific determined deficit. In FIG. 1B, the electrical stimulator system 104 is a neuro-stimulator 140 that provides constant stimulation to a healthy node to compensate for a damaged node to address neglect, which is one form of a brain deficit. In FIG. 1B, the brain 102 includes a damaged posterior parietal cortex node 130, the lateral intraparietal area (LIP), which is an area that is responsible for eye movements and attention. As will be explained below, a node in the thalamus known as a pulvinar region 132 may also be stimulated to compensate for inactivation of the node 130. The neuro-stimulator 140 is implanted with an electrode 142 that may stimulate the superior temporal sulcus (STS), frontal eye field (FEF), prefrontal cortex or pulvinar 132, or other nodes in the cortical eye movement circuit to compensate for the damage to the posterior parietal cortex node LIP 130.

An example neurostimulator 140 may be a dual-channel device, which may deliver bilateral stimulation. The neurostimulator 140 is coupled to a battery 144 and includes circuits to deliver a controlled electrical pulse to precisely targeted areas of the brain via the electrode 142. Additional electrodes may be used to deliver electrical pulses to other nodes required to bypass a damaged node.

Figure 1C:
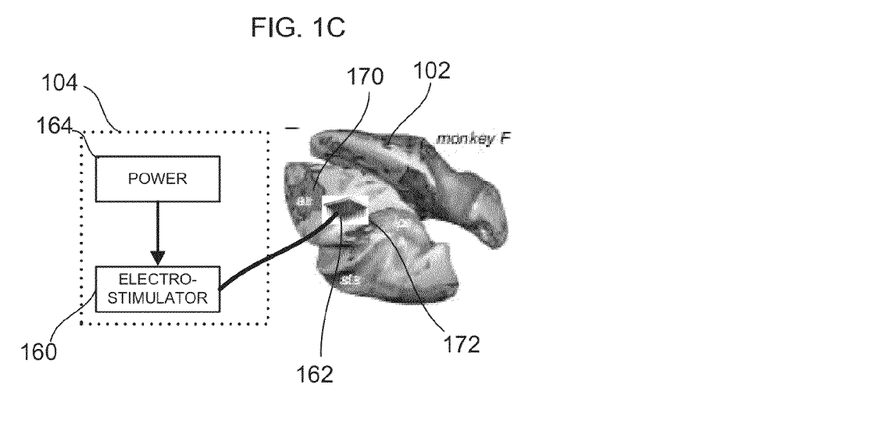
FIG. 1C is a block diagram of an alternate system having an electrode array to provide patterned stimulation to address more refined stimulation to recover function.

FIG. 1C is an alternate patterned stimulation arrangement for the electrical stimulator system 104. The electrical stimulator system 104 in FIG. 1C includes an electro-simulator 160 having connections to an electrode array 162 and a battery 164. The electrode array 162 in this example includes approximately 100 microelectrodes for intracortical microstimulation. Patterned stimulation can be particularly useful to address brain deficits such as damage to an anterior intraparietal (AIP) node 170 to provide therapy for apraxia, a deficit in properly shaping the hand to grasp an object. Stimulation is delivered to a ventral premotor cortex (PMv) node 172, a major recipient of area AIP projections. The patterned stimulation from the electrode array 162 mimics the input from the damaged AIP node 170, thus substituting the output of the AIP node to the PMv node.

Figure 1D:
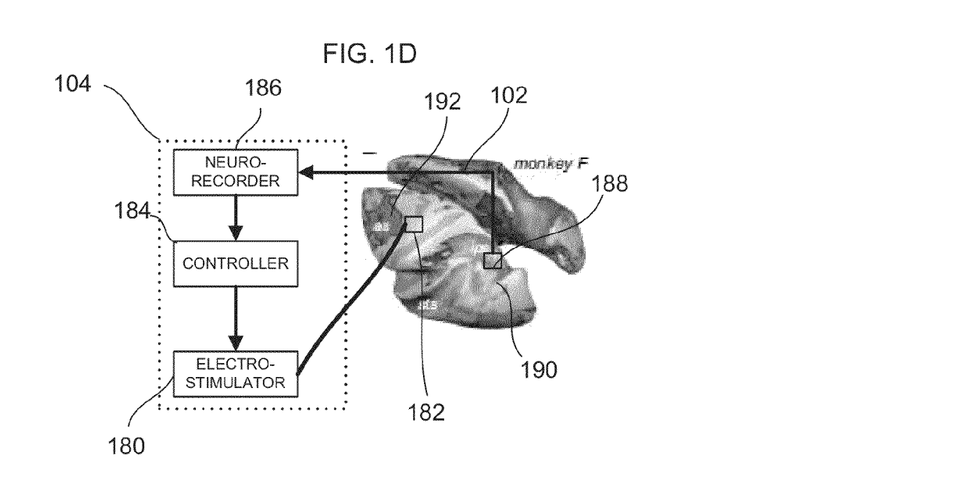
FIG. 1D is a block diagram of an alternate system having an electrode array, a recorder and a controller, to record signals from an input node to a damaged node and stimulate a node that normally receives output from the damaged node.

FIG. 1D is an alternative patterned stimulation arrangement for the electrical stimulator system 104. The electrical stimulator system 104 in FIG. 1D includes an electro-stimulator 180 coupled to an electrode 182, a controller 184, and a neuro-recorder 186 coupled to a sensor 188. In this example, damage to the parietal reach region (PRR) causes optic ataxia, the inaccurate reaching to visual targets in space. The neuro-recorder 186 is attached to the sensor 188, which is coupled to a parieto-occipital (PO) area 190, a region that provides visual input to the PRR. The recorded signals from the PO area 190 are used to bypass the PRR and the controller 184 reads the recorded signals from the neuro-recorder 186 and controls the electro-stimulator 180 to provide electrical intracortical microstimulation via the electrode 182 to a dorsal premotor cortex (PMd) node 192, which normally receives input from the PRR. In such a manner, the electrical stimulator system 104 replaces the PRR and allows normal functioning to address optic ataxia.

As these examples show, the system 100 may be used to train the network of brain circuits via constant stimulation such as in FIG. 1B or phased stimulation, or pattern stimulation as in FIG. 1C or 1D for the purpose of providing signals to downstream areas from the damaged node.

Figure 2A:
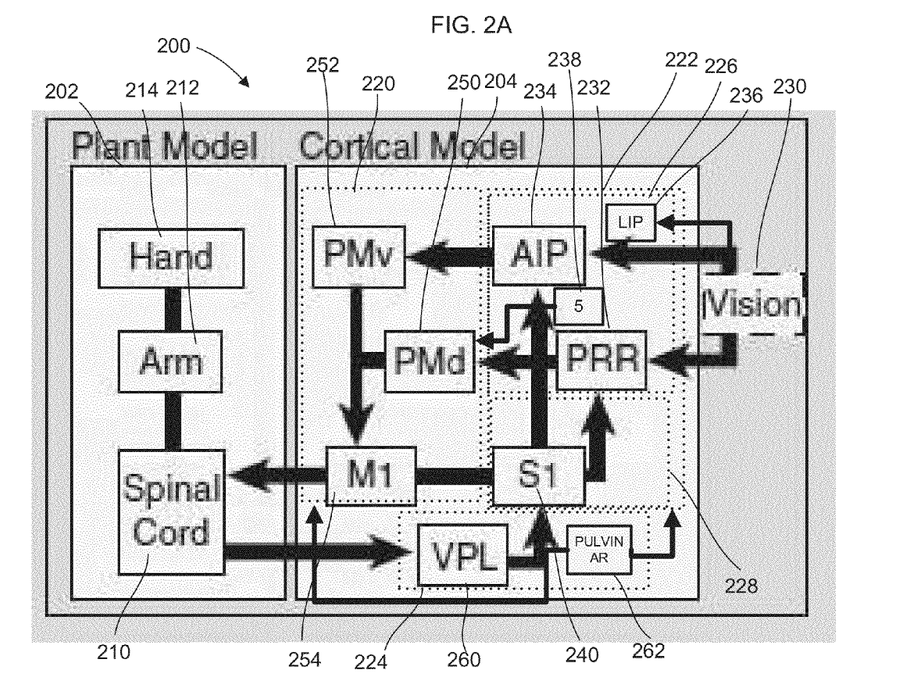
FIG. 2A is a block diagram of a model of the nodes of the brain for reach and grasp movements.
Figure 2B:
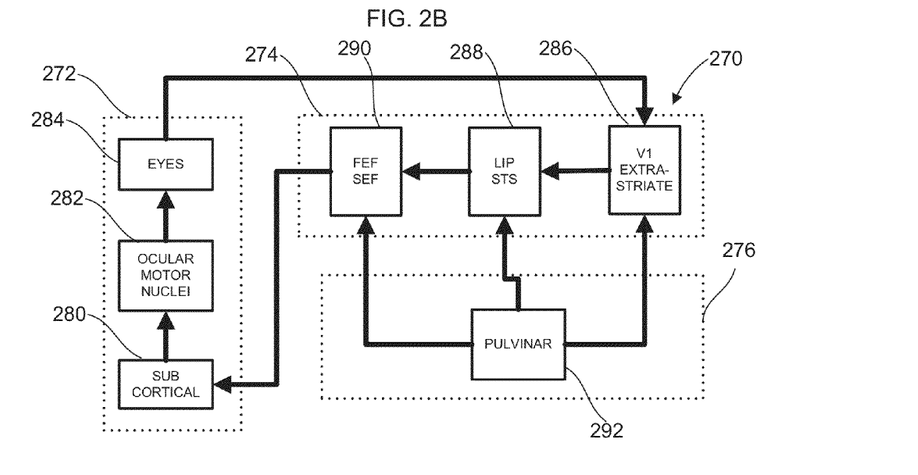
FIG. 2B is a block diagram of the nodes of the brain for eye movements.

FIGS. 2A and 2B are block diagrams of the sensorimotor system of a brain. The block diagrams in FIGS. 2A and 2B are based on the sensorimotor system of nonhuman primates as a model system because it shares common features with the human nervous system. FIG. 2A shows a basic circuit 200 for sensory to motor processing for reach and grasp in the primate brain. FIG. 2B shows a basic circuit 270 for saccadic eye movements.

The circuit 200 in FIG. 2A is divided into a plant model 202 and a cortical model 204. The plant model 202 includes a spinal cord 210 that sends signals through nerves to activate muscles in an arm 212 and a hand 214 for reaching and grasping motions as will be explained below. The cortical model 204 represents various circuits in the brain and includes a frontal lobe 220, a parietal lobe 222, and a thalamus region 224. The parietal lobe 222 is divided into a posterior parietal cortex (PPC) 226 and an anterior parietal cortex (APC) 228.

The block diagram of the circuit 200 is the cortical organization of movement as described from its anatomical and physiological basis. FIG. 2A shows that there is a great deal of complex connectivity, including both feedback and feed-forward paths, involved in initiating and executing movements of the upper arm 212. Such a model may be used by the system 100 to determine stimulation of different nodes to compensate for damage from other nodes in the basic brain circuits, lobes 220 and 222.

A quantitative understanding of the neural activity and its origins from each of the cortical regions and further quantitative analysis of the connectivity among different regions will allow building in silico models of the cortex such as the model 118 in FIG. 1, which may be used to determine the proper nodes to stimulate in response to damage in other nodes. The cortical model 204 is coupled to a visual input 230 such as extrastriate cortical areas including the parieto-occipital (PO) area, which sends signals to a parietal reach region (PRR) 232, an anterior intraparietal area (AIP) 234, a lateral intraparietal area (LIP) 236, and a somatosensory association cortex (Area 5) 238, which are all part of the PPC 226. The APC 228 includes a primary somatosensory cortex (S1) 240. The frontal lobe 220 includes a dorsal premotor cortex (PMd) 250 and a ventral premotor cortex (PMv) 252, which converge onto a primary motor cortex (M1) 254. The primary motor cortex 254 sends commands to the spinal cord 210 in the plant model 202. The thalamus 224 includes a somatosensory thalamus (VPL) 260 and a pulvinar region 262.

Sensory information for dexterous movements is derived in large part from vision and somatic sensation including touch and the sense of limb position. Visual inputs into the cortical circuits for reaching and grasping first arrive in large part in the parietal reach region (PRR) 232 and the anterior intraparietal area (AIP) 234, both within the posterior parietal cortex (PPC) 226. Somatosensory signals enter the circuit a bit more directly as projections from the somatosensory thalamus (VPL) 260 to the primary somatosensory cortex (S1) 240 and later the PRR 232 and AIP 234. Reaching and grasping are processed, to a large extent, separately in the primary somatosensory cortex (S1) 240 with reaching encoded by the PRR 232, area 5 node 238, and the dorsal premotor cortex (PMd) 250 and grasping encoded by the AIP 234 and ventral premotor cortex (PMv) 252. These areas converge onto the primary motor cortex (M1) 254 that issues commands for movements to the spinal cord 210, which in turn drives the muscles in the arm 212 and the hand 214.

The simple act of reaching out to grasp a coffee cup requires the brain to assess the size and shape of the cup and plan how fingers will shape to grasp the cup. Although the hand shapes to match the cup during the reach motion, once the hand touches the cup, sensation from the fingertips also contributes to controlling how the hand grasps, lifts, and handles the cup so that a subject can drink from the coffee cup.

Information about the shape of objects seen is processed by the AIP 234 in the parietal lobe 222 of the cerebral cortex model 204 in FIG. 2A. When objects are to be grasped with the hand, the AIP 234 sends relevant shape information to another cortical area, the PMv 252 in the frontal lobe 220. Here the shape information is translated into the necessary conformation of the fingers, and this information is sent to the primary motor cortex (M1) 254, which executes the appropriate grasp. Once the fingers contact the object, sensory information from the fingers ascends from the spinal cord 210 through deeper parts of the brain arriving in the somatosensory thalamus (VPL) 260 and then in the somatosensory cortex (S1) 240. Sensory information from the primary somatosensory cortex (S1) 240 can then guide the primary motor cortex (M1) 254 in handling the object without dropping it.

In particular, the parts of the brain that plan dexterous reaching and grasping are of interest. In order to determine nodes for stimulation, activity from the various brain circuits involved in forming and executing these plans are monitored while parts of the circuits were temporarily inactivated by applying pharmacological agents that produce local inhibition simulating damage to these parts. The advantages of this technique, besides not producing any harm to the test animals, include being able to produce highly localized inactivations of neural circuits that allow the fine functional dissection of neural networks in the brain. This and other data were used to inform and validate computational models of the healthy and injured nervous system for treatment by the system 100 and providing the nodes for stimulation to compensate for inactive nodes in the brain.

FIG. 2B shows a basic circuit 270 for saccadic eye movements. The circuit 270 in FIG. 2B is divided into a plant model 272, a cortical circuit 274, and a thalamus region 276. The plant model 272 includes a sub cortical region 280 that sends signals through ocular motor nuclei 282 to activate an eye 284. The visual stimulation from the eyes 284 are sent to a primary visual cortex (V1) and extrastriate visual cortex 286. These visual signals are input to areas in the LIP and areas within the superior temporal sulcus (STS) 288, which are parts of the PPC, which are important for sensorimotor transformation. These PPC areas 288 then project to frontal lobe areas 290 involved in eye movements (e.g., FEF, supplementary eye field (SEF)), which then project to eye movement centers in the midbrain. The cortical areas in both the frontal and parietal lobe areas 290 and 288 are influenced by a pulvinar region 292 of the thalamus 276. The cortex provides input to midbrain structures, which in turn provide input to the oculomotor nuclei 282 that innervate the eye muscles and generate movement of the eyes 284. Visual information after the eye movement is then sent back to the primary visual cortex (V1) and extrastriate visual cortex 286.

Four distinct neurological deficits, neglect, apraxia, hemianesthesia, and optic ataxia, occurring frequently in humans may be treated by use of the system 100 in this example. The computational models may be used to account for the appearance of these deficits in animal models and to suggest the clinical strategies of stimulating healthy nodes to recover the function of damaged nodes causing the deficits. The system 100 applies such models to execute the clinical strategies by stimulating healthy nodes in the brain to cure such neurological deficits.

Neglect is a condition in which patients can see and move but are not consciously aware of the side space opposite to the lesioned hemisphere and do not make voluntary movements into that half of the space. Apraxia is a movement abnormality in which a subject is unable to handle objects appropriately, while still being able to recognize the object and know its use, having no loss of strength or dexterity in the hand. Injuries to the parietal lobe 222 of the cerebral cortex that damage the AIP 234 in FIG. 2A may result in apraxia. Hemianesthesia is a deficit resulting from the loss of hand sensation. Optic ataxia is a condition in which patients cannot connect the perceived location of visual stimuli with the planning of accurate movements, as if vision has been disconnected from movement. One remarkable problem for optic ataxia patients is their grossly inaccurate reaches to seen objects. Optic ataxia may result from damage to either the PRR 232 or the area 5 node 238 in FIG. 2A.

Neglect is commonly a result of damage to the posterior parietal cortex (PPC) 232 shown in FIG. 2A. An animal model of neglect is developed by inactivating of the LIP 236 or the PRR 232 in the PPC 226 and the pulvinar region 262, the region of the thalamus 224 that has direct connections with the PPC 232. For LIP inactivation, in a free choice task, the test animals were biased and generally did not choose targets in the neglected visual field. Activity was recorded using functional magnetic resonance imaging (fMRI), in which the changes in blood flow related to changes in neural activity are measured. A great power of this technique is that it can image brain activity in the whole brain in a matter of seconds. Activity can also be recorded by measuring neural activity directly using arrays of implanted microelectrodes.

As explained above, one application of the system 100 is for repair of the deficit of neglect as in the configuration shown in FIG. 1B. Patients ignore or are not aware of the contralateral space, particularly left space for right parietal damage. A popular competition theory has been proposed for neglect in which the two cerebral hemispheres each process information in the contralateral space and then compete with one another for the distribution of attention and awareness. If one hemisphere is damaged then the other has an advantage and the patient is biased toward the healthy visual field and unable to process information in the unhealthy part of space.

One study is an animal model of neglect in the eye movement circuit that includes the lateral intraparietal area (LIP) in the PPC cortex 288 within the superior temporal sulcus (STS) and areas in the frontal lobe 290 including the frontal eye fields (FEF), supplementary eye fields (SEF), and the prefrontal cortex 274 in FIG. 2B.

Eye movements are tightly connected to attention and these same areas are also responsible for orienting attention. Temporary pharmacological inactivation of the LIP 236 in non-human primates (NHPs) produced a form of neglect termed extinction which lasted for several hours. Extinction is a condition in which a competing stimulus in the healthy field biases the selection of a target for a saccade (fast eye movement) toward the healthy field and away from the unhealthy field. During these behavioral experiments the NHPs were imaged for changes in blood oxygen level dependent (BOLD) signal reflecting changes in brain activity using fMRI.

When single targets were presented in an instructed trial there was reduced activity in the inactivated eye movement circuit in the one hemisphere (consistent with the biased competition model) but not increased activity in the non-inactivated hemisphere (not consistent with the biased competition model). In the condition of free choice between two stimuli, one in the healthy field and one in the unhealthy field, the animals usually chose the stimulus in the healthy field. Sometimes the NHPs were able to overcome the deficit, and chose the stimulus in the unhealthy field. On these occasions there was increased activity in both hemispheres. It is as if additional effort is exerted in both hemispheres to rebalance activity between them. Thus, this study demonstrates potential stimulation therapies that would rebalance the activity between hemispheres and "cure" neglect.

One example approach to address neglect is to stimulate another cortical node in the lesioned eye movement circuit, such as the FEF in the frontal lobe 290 or the STS at the junction of the PPC and the temporal lobe 288 as shown in FIG. 2B, to balance activity between the hemispheres. A second is to stimulate the dorsal pulvinar 292, a region of the thalamus 276 that is connected to all cortical nodes in the eye movement circuit 270. Bilateral stimulation of the cortex or pulvinar might be even more effective in balancing activity. As explained above, the implanted electrical stimulation system 104 in FIG. 1B may be used for constant stimulation of these regions.

Temporary stimulation may provide learning effects that make the relief more permanent and does not require constant stimulation. Inactivation of the pulvinar produces extinction similar to inactivation of the LIP but more pronounced. fMRI studies show a decrease in the cortical circuit in the same hemisphere as the inactivated pulvinar, and increased activity in the other hemisphere, consistent with the competition model. The extinction after pulvinar inactivation can be greatly reduced if the target in the affected visual field indicates a larger reward if selected. Neural activity in the cortical circuits increases with increase in the amount of expected reward. This result strongly suggests that pulvinar or cortical stimulation, by increasing activity in the circuits similar to high reward expectation, should "cure" neglect. The concepts may be applied to other neurological deficits. In other studies, deficits in reach behaviors were found with inactivation of other subdivisions of the PPC. These deficits include misreaching (optic ataxia) and difficulty in making on-line corrections during reaches. These deficits may also be corrected by stimulation in other parts of the reach circuit.

Figure 3:
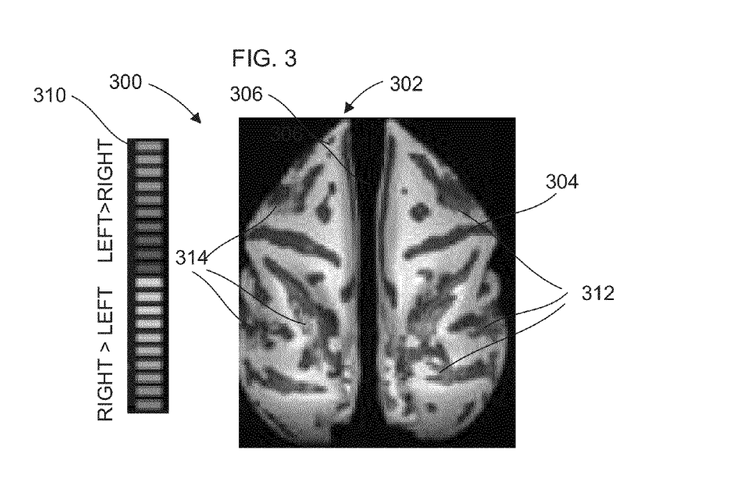
FIG. 3 is an fMRI image of an example animal brain showing healthy nodes for eye movement.

FIG. 3 is an fMRI image 300 showing the cortex of a non-human primate 302. The brain 302 includes a right cerebral hemisphere 304 and a left cerebral hemisphere 306. The image 300 shows the eye movement activity in the cerebral cortex for leftward eye movements, which activates the eye movement circuit in a right hemisphere 304, and rightward eye movements, which activates a left hemisphere 306. As shown by the scale 310, left eye movements produce greater activity in the right hemisphere 304 (shown in blue areas to green areas 312), and right eye movements produce greater activity in the left hemisphere 306 (shown in yellow areas to red areas 314).

A disadvantage of fMRI is that the temporal and spatial resolution is not as great as recording the electrical activity of single neurons. An alternative approach would be to implant a large number of electrodes (e.g., 500) in different nodes of the circuit to obtain a more precise picture of the pattern of activity required for repair.

Injuries to the parietal lobe 222 of the cerebral cortex that damage the AIP 234 can cause apraxia where the patient is unable to handle objects appropriately, while still being able to recognize the object and know its use, having no loss of strength or dexterity in the hand.

Using neural signals recorded painlessly from the AIP 234, the PMv 252, the M1 254, and the S1 240 shown in FIG. 2A in non-human primates as they reach and grasp various objects, a computer model may be built of how the brain identifies the shape of objects visually and adjusts the shape of the hand to match. Then, by reversibly inactivating the AIP 234, temporary apraxia may be induced. While the apraxia is present, biomimetic micro-stimulation may be delivered to the PMv 252 to confirm that stimulation to the PMv 252 effectively repairs the apraxia. Thus apraxia may be cured by stimulating the PMv 252 via the electrical stimulator system 104 in FIG. 1A.

Damage to the ascending somatosensory signals from damage to the ventral posteror-lateral nucleus (VPL) of the thalamus will interrupt somatosensory signals coming from the spinal cord en route to the primary somatosensory cortex (S1) producing the loss of somatosensory sensation (hemianesthesia). This loss of sensation could potentially be restored by patterned stimulation of S1 via the electrical stimulator system 104 in FIG. 1C or 1D.

An animal model of optic ataxia has also been developed by Hwang, et al., 2012. Inactivation of the PRR 232 produces mis-reaching of the animals in the space opposite the inactivated hemisphere thus providing a starting point for addressing deficits as simulated by the inactivation of the PRR 232. The network is imaged and recorded for evaluation of potential electrical stimulation therapies similar to the treatment of neglect. Thus, optic ataxia may be addressed by stimulating the dorsal premotor cortex PMd node 250.

The modeling of neural activity associated with movement by a number of signal processing and modeling tools such as control theory, biomimetic models, and Bayesian inference may be applied to determine the normal functioning of the circuit, the changes in activity due to damage to nodes in the circuit, and used to guide electrical stimulation to repair the circuit.

The control problem that the brain must solve is strongly influenced by the complex circuitry of the spinal cord and the nonlinear mechanical properties of the musculoskeletal system. A great deal of information is available about these individual elements. This information can be used along with the neural models to predict the behavioral deficits from a lesion and strategies of stimulating other nodes to repair these deficits.

Figure 4:
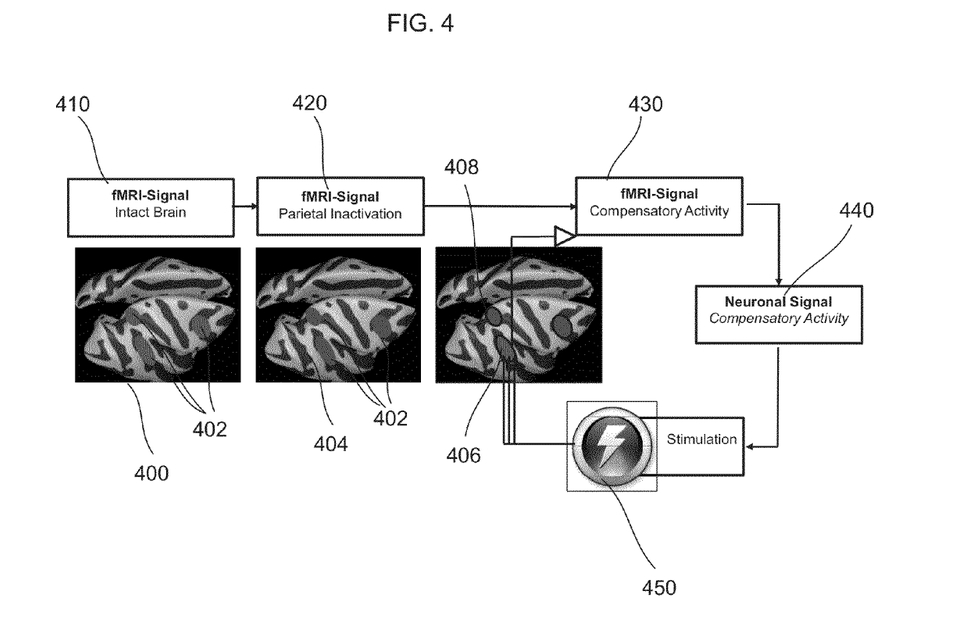
FIG. 4 is a flow diagram of the process of determining a model and developing stimulation to compensate for a damaged brain node.

FIG. 4 is a flow diagram of the process of the detection and repair for brain deficits performed by the system 100 in FIG. 1. The fMRI imager 110 is used to produce an image 400 of activity in the healthy parietal nodes 402 of the brain 102 (410). The nodes in the parietal region are then inactivated and the fMRI imager 110 is used to produce an image 404 of the activity in the inactivated brain nodes 402 (420). The images 400 and 402 from the fMRI imager 110 are then used to determine the nodes for which stimulation may be applied to compensate for the damaged node (430). This data is used to program the electrical stimulation system 104, which is implanted in order to provide stimulation to the healthy nodes (440). The stimulation is then applied to a healthy node 406 to compensate for damaged nodes 408. (450).

Each of these embodiments and obvious variations thereof is contemplated as falling within the spirit and scope of the claimed invention, which is set forth in the following claims.

What is claimed is:

1. A method of brain repair of a damaged node, comprising:
   determining the location of a damaged node within a brain circuit;
   determining at least one functioning node to compensate for the damaged node within the brain circuit;
   placing a stimulator on the brain on the at least one functioning node to bypass the activity from the damaged node to compensate for the damaged node; and
   stimulating the at least one functioning node to compensate for the damaged node.

2. The method of claim 1, wherein the stimulator placement is performed using functional magnetic resonance imaging studies.

3. The method of claim 1, wherein the stimulator placement is performed using studies of similar deficits.

4. The method of claim 1, wherein the stimulator placement is performed using neural recording studies.

5. The method of claim 1, wherein the stimulator provides a constant stimulus.

6. The method of claim 1, wherein the brain circuit is damaged from a neurological deficit.

7. The method of claim 6, wherein the neurological deficit is neglect, the brain circuit is the parietal lobe, the damaged node is the posterior parietal cortex node and the functioning node is the pulvinar.

8. The method of claim 6, wherein the neurological deficit is apraxia, the brain circuit is the parietal node, the damaged node is the anterior intraparietal area and the functioning node is the ventral premotor cortex.

9. The method of claim 6, wherein the neurological deficit is hemianesthesia, the brain circuit is the parietal node, the damaged node is the somatosensory thalamus and the functioning node is the primary motor cortex.

10. The method of claim 6, wherein the neurological deficit is optic ataxia, the brain circuit is the parietal node, the damaged node is the parietal reach region or area 5 and the functioning node is dorsal premotor cortex node.

11. The method of claim 1, further comprising:
    recording signals from an activating node in the brain circuit transmitted to the damaged node; and
    activating the stimulation to the node when the recorded signal is received.

12. The method of claim 1, wherein the stimulator is an electro-stimulator having an electrode.

13. The method of claim 1, wherein the stimulator is an optogenetic stimulator having an optical fiber.

14. A system for compensating for a damaged node of a brain circuit, the system comprising:
    a storage device including data associated with a brain circuit having the damaged node;
    a controller coupled to the storage device to select a healthy node to stimulate to bypass the damaged node based on the data associated with the brain circuit and a model of the brain circuit; and
    a stimulator for stimulation of the selected healthy node of the brain circuit, the stimulator operable to stimulate the healthy nodes to bypass the function of the damaged node.

15. The system of claim 14, wherein the stimulator includes an electro-stimulator having an electrode.

16. The system of claim 15, wherein the electrode is part of an electrode array.

17. The system of claim 14, wherein the stimulator includes a neural recorder to record signals from the brain circuit and a stimulator controller to control electrodes to apply a stimulation pattern in accordance with the recorded signals from the neural recorder.

18. The system of claim 14, wherein the stimulator is an optogenetic stimulator having an optic fiber.

19. The system of claim 14, wherein the damaged node is result of at least one of neglect, apraxia, hemianesthesia, or optic ataxia.

20. The system of claim 14, further comprising a functional magnetic resonance imager, wherein the data associated with the brain circuit is derived from a functional magnetic resonance image of the brain circuit taken by the functional magnetic resonance imager.

21. The system of claim 14, further comprising a neural recorder, wherein the data associated with the brain circuit is derived from a neural recording of the brain circuit taken from the neural recorder.

22. The system of claim 14, further comprising an optical recorder, wherein the data associated with the brain circuit is derived from optical recording of populations of neurons with a node of the brain circuit.

\* \* \* \* \*